United States Patent [19]

Attias et al.

[11] Patent Number: 6,051,669

[45] Date of Patent: Apr. 18, 2000

[54] POLYMERS FROM CERTAIN CONJUGATED ORGANIC COMPOUNDS

[75] Inventors: André-Jean Attias; Bertrand Bloch, both of Paris; Chantal Cavalli, Voisins le Bretonneux, all of France

[73] Assignee: Office National d'Estudes et de Recherches Aerospatiales (ONERA), Chatillon, France

[21] Appl. No.: 09/122,718

[22] Filed: Jul. 27, 1998

Related U.S. Application Data

[62] Division of application No. 08/943,112, Oct. 3, 1997.

[30] Foreign Application Priority Data

Oct. 3, 1996 [FR] France ................................. 96 12066

[51] Int. Cl.[7] .................................................. C08F 26/06
[52] U.S. Cl. ........................... 526/248; 258/261; 258/265
[58] Field of Search ..................... 526/248, 258, 526/261, 265

[56] References Cited

U.S. PATENT DOCUMENTS 4,841,009  6/1989  Kelsey ...................................... 528/75

OTHER PUBLICATIONS

Igeta, H. et al, "Studies on Pyrazines. XV. N–Oxidation of 3,3'–Bipyrazines and Reactions of their N–Oxides", Chemical and Pharmaceutical Bulletin, vol. 18, No. 7, 1970, pp. 1340–146.

*Primary Examiner*—Bernard Dentz
*Attorney, Agent, or Firm*—Jacobson, Price, Holman & Stern, PLLC

[57] ABSTRACT

The invention relates to conjugated compounds of general formula (I)

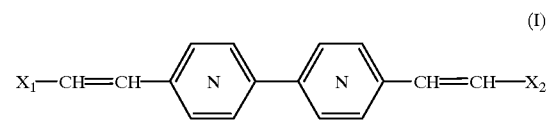

wherein $X_1$ and $X_2$ are, independently of one another, electron-withdrawing or electron-donating systems, and to a process for the preparation of these compounds.

The invention also relates to any material which includes the compounds of general formula I and to the use of said compounds or of any material which includes them in electronic, optoelectronic, nonlinear optical and electrooptical devices.

4 Claims, No Drawings

POLYMERS FROM CERTAIN CONJUGATED ORGANIC COMPOUNDS

This is a division of application Ser. No. 08/943,112, filed Oct. 3, 1997 now U.S. Pat. No. 5,872,255.

The present invention relates to new conjugated organic compounds of general formula I:

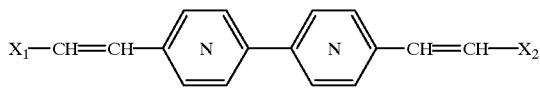

(I)

wherein $X_1$ and $X_2$ are, independently of one another, conjugated aliphatic systems themselves conjugated with the remainder of the molecule, or aromatic cyclic or aromatic heterocyclic systems, in particular a phenyl or a thienyl, which are unsubstituted or substituted one or more times with radicals chosen from the following group: alkyl, halo, phenyl, naphthyl, hydroxyl, alkoxy, amino, lower alkylamino, lower dialkylamino, lower alkyl(lower alkoxy)amino, (lower alkylacyl) aminocarbonyl, lower alkylcarbonyl, lower alkoxycarbonyl, carboxyl, (lower alkylamino) carbonyl, (lower dialkylamino) carbonyl, halocarbonyl, trifluoromethyl, nitro, nitroso, cyano, 2,2-dicyanovinyl, 3,3-dicyanoprop-2-enyl, tricyanovinyl, dicyanomethylidenyl, mercapto, alkylthio, sulfino, alkylsulfonyl, sulfo, alkylsulfonyloxy, alkylsulfinyl, pyridinyl and conjugated pyridinyl derivatives.

Lower alkyl is understood to mean linear or branched alkyl radicals comprising 1 to 6 carbon atoms.

The entity

represents a nitrogenous aromatic heterocyclyl radical comprising 1 to 4 nitrogen atoms chosen from pyridinyl, pyrazinyl, pyrimidinyl or triazinyl and containing at least one nitrogen atom in the α position with respect to the CH=CH double bond.

In particular, the present invention comprises the compounds of general formula I wherein the entity

represents a pyridinyl radical containing a nitrogen atom in the α position with respect to the CH=CH double bond and wherein $X_1$ and $X_2$ represent, independently of one another, preferably a phenyl, a 4-cyanophenyl or a 4-hydroxyphenyl.

The present invention relates to the preparation of the compound of general formula I, in particular 6-($X_1$—CH=CH)-6'-($X_2$—CH=CH)-3,3'-bipyridine. The operating conditions of the process for the preparation according to the invention of the compound of general formula I vary according to the nature of the $X_1$ and $X_2$ substituents.

If $X_1 = X_2$, the product of general formula II

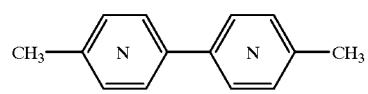

(II)

wherein the entity

represents a nitrogenous aromatic heterocyclyl radical comprising 1 to 4 nitrogen atoms chosen from pyridinyl, pyrazinyl, pyrimidinyl or triazinyl and containing at least one nitrogen atom in the α position with respect to the methyl radical, is condensed with an excess of aldehyde of formula X—CHO with $X = X_1 = X_2$, $X_1$ and $X_2$ being defined as above.

In contrast, if $X_1 \neq X_2$, the product of general formula II, wherein the entity

has the same meaning as above, is successively condensed with a molar equivalent of aldehyde of formula $X_1$—CHO, wherein $X_1$ is defined above, and then with a molar equivalent of aldehyde $X_2$—CHO, wherein $X_2 \neq X_1$ and $X_2$ is defined above. The reaction can be carried out in the presence of a catalyst and, optionally, of a dehydrating agent. The same compound, such as benzoic anhydride, can carry out both the abovementioned functions.

This condensation reaction, known under the name of Knoevenagel reaction, is described in Ber., 31, 2596 (1898) and Journal of Polymer Science, A1(7), 743, 752 (1969). It is greatly influenced by the nature of the $X_1$ and $X_2$ substituents of the aldehydes used. An electron-withdrawing substituent will promote the reaction whereas an electron-donating substituent will decrease the yield thereof.

On the molecular scale, the compounds according to the invention exhibit numerous properties. The very structure of these molecules confers on them a π-electron system which is highly delocalized over a relatively great length. The asymmetric nature of this electron delocalization can be induced by a careful choice of the $X_1$. and $X_2$ substituents; if $X_1$ is chosen from the group of electron-donating substituents and $X_2$ is chosen from the group of electron-withdrawing substituents, the polarity and especially the polarizability of the compounds according to the invention is thereby found to be greatly increased and the said compounds exhibit nonlinear optical properties.

The nature of the $X_1$ and $X_2$ substituents makes it possible to confer, on the compounds according to the invention, the appropriate reactivity for the purpose of their incorporation in polymers or of their homo- or copolymerization. Finally, the compounds according to the invention are mesomorphic and benefit from high thermal stability.

Depending on the choice of the $X_1$ and $X_2$ substituents, the compounds of general formula I exhibit a combination of structural and functional properties which make them excellent candidates as active constituents of electronic, optoelectronic, nonlinear optical or electrooptical devices.

The compounds of general formula I according to the invention exhibit advantageous properties on the molecular scale. It is thus essential for the materials deriving from the said compounds and participating in the production of the abovementioned devices to retain these properties on the macroscopic scale.

The present invention relates to materials deriving from the compounds according to the invention. Four classes of materials will be distinguished:

Molecular materials composed of the compounds of general formula I used as is: monocrystals, Langmuir-Blodgett monomolecular layers, molecular sandwich, molecular wire or compound included in an organic (thermoplastic polymer, for example) or inorganic (glass, as described in EP-A-0,304,051, published on 22.02.1989, ceramic or sol-gel matrix, as described in FR 2,675,S09, published on 23.10.1992) host-matrix; in the case where the compounds according to the invention are unreactive chemically.

Polymer materials, in particular polyolefin, polyester, polyimide, poly(vinyl acetate), poly(vinyl chloride), polyurethane, poly(methyl methacrylate) or hydroxyethylcellulose, on which the compounds according to the invention are grafted as side chains; in the case where the compounds exhibit a functionality greater than or equal to 1.

Two routes for the preparation of the material are possible: the compound is either grafted onto the constituent units of a homopolymer or of a copolymer, as described in Polymer, 36(24), 4561 (1995), or grafted onto a monomer which is then polymerized or copolymerized.

Polymer or copolymer materials obtained by polymerization or copolymerization of the compounds of general formula I, in the case where the said compounds have a functionality greater than or equal to 2.

Metal complexes obtained by complexation of one or more molecules of general formula I.

Any molecular engineering strategy which makes it possible to optimize the properties of the material on the microscopic and macroscopic scale will be developed first by choosing the nature and the reactivity of the $X_1$ and $X_2$ substituents and then by choosing the most suitable forming process for the application targeted by the device.

The present invention relates to the use of the compounds and of the materials according to the invention as active constituents of electronic, optoelectronic, nonlinear optical and electrooptical devices.

As has been mentioned above, the compounds according to the invention exhibit a highly delocalized π-electron system; these compounds can thus participate in the production of conductive or semi-conductor molecular materials for purely electronic devices but also in the production of electroluminescent or photoconductive molecular materials for optoelectronic devices (optoelectronic device will be understood to mean any optically-controlled electrical modulator or generator).

The conductive or semi-conductor materials according to the invention, put into a form so that they exhibit a nonlinear current-voltage characteristic, optionally in combination with rectifying and/or memory effects, are advantageous as active components in the production of electronic devices, for example diodes and transistors.

The electroluminescent materials according to the invention can participate in the production of light-emitting diodes (LED) of use in active display devices, as described in J. H. Burroughes et al., "Nature", 347, 1990, page 539. In particular, the compound of general formula I grafted as side chain onto a polyester makes it possible to obtain an electroluminescent polymer, the forming process of which, for the production of an LED, is easy.

The photoconductive materials according to the invention, for example the polymerized compound of general formula I or the compound of general formula I grafted as side chain onto a polymer, make possible the recording of electrostatic images of use in image reproduction, for example xerography, photocopying or laser printing. Patent FR 2,712,893, published on 02.06.1995, describes a grafted silane polymer film which makes such applications possible. The said photoconductive materials, combined in series with a liquid crystal film, across the terminals of which a voltage is applied, define an optically-addressed spatial light modulator capable of converting incoherent light into coherent light or of converting infrared radiation into visible light and vice versa.

As has been mentioned above, the compounds according to the invention exhibit a π-electron system which is delocalized over the whole of the conjugated molecule. This delocalization can be reinforced by the interactive effect of an electron-donating group, for example $X_1$, and of an electron-withdrawing group, for example $X_2$, each placed at the chain end. The electron cloud thus polarized interacts with an electromagnetic field of angular frequency $\omega_o$ in order to induce a nonlinear optical response, for example an electromagnetic field of angular frequency $\omega \neq \omega_o$. Such compounds make possible the use of nonlinear optical devices, it being known that a good material for such devices should not only incorporate the said non-centrosymmetric compounds according to the invention but also incorporate them non-centrosymmetrically: the compound of general formula I, such that $X_1=NH_2$ and $X_2=NO_2$, grafted onto a polyimide provides a material which meets these requirements.

The interactions of the materials and compounds according to the invention with the incident angular frequency or frequencies can be different in type: doubling the incident frequency (application to high-density optical memory devices), addition or difference of two incident frequencies (application to infrared-visible converters and to optical rectifiers), or parametric amplification or emission (application to tunable coherent sources and to parametric lasers). These various processes make it possible to generate new frequencies from the incident frequency or frequencies over a spectral range from the near UV to the near IR. If in addition the nonlinear optical material according to the invention is subjected to a low-frequency electrostatic or electromagnetic field, the incident angular frequency/material interaction will have the effect of modifying not only the incident frequency of the incident wave but also its amplitude, its phase and its path: the nonlinear optical compounds according to the invention can participate in the production of electrooptical devices (electrooptical device will be understood to mean any electrically-controlled optical modulator or generator), in particular electrooptical switches and modulators of use in the treatment of the optical signal and optical telecommunications.

Finally, as has been mentioned above, the compounds according to the invention exhibit a mesomorphic nature which makes it possible to envisage their application in passive liquid-crystal display electrooptical devices.

The following examples will illustrate the invention without limiting the scope thereof.

EXAMPLE 1

Preparation of 6,6'-distyryl-3,3'-bipyridine 2.7 g of 6,6'-dimethyl-3,3'-bipyridine (DMBP) i.e. $1.5 \times 10^{-2}$ mol, 6.5 g ($6.3 \times 10^{-2}$ mol) of benzaldehyde and 7.9 g ($3.5 \times 10^{-2}$ mol,) of benzoic anhydride, acting both as catalyst and as dehydrating agent, are successively introduced into a 50 ml two-necked round-bottomed flask. The mixture, heated on an oil bath to 200° C., is left at reflux under a slight stream of inert gas for 1.5 hours, the progress of the reaction being followed by exclusion chromatography. After the time indicated, the DMBP has completely disappeared and the mixture is no longer changing. The reaction mixture is washed with ethanol and with ether. The residue, dark brown in color, is recrystallized from toluene; 1.7 g of a still brownish product are thus obtained. A 98% pure product is obtained by further crystallization from toluene in the presence of active charcoal. Amount obtained: 1.43 g ($0.4 \times 10^{-2}$ mol); yield: 27%).

The compound obtained, which is a substance crystallized in the form of light-yellow-colored flakes with a slightly fluorescent appearance, has the distinguishing feature of giving rise above 238° C. to the formation of a liquid crystal phase of smectic A 35 type, which is itself converted from 280° C. into a nematic phase, itself melting at 311° C. In solution, this compound is effectively fluorescent, with an emission maximum at 424 nm, whereas the absorption peak is at 350 nm.

EXAMPLE 2

Preparation of 6,6'-di(4-cyanostyryl)-3,3'-bipyridine

The same operating conditions are used as in Example 1.

The mixture, composed of 1.18 g of 6,6'-dimethyl-3,3'-bipyridine (DMBP), i.e. $6.4 \times 10^{-3}$ mol, 3.57 g of 4-cyanobenzaldehyde ($27.2 \times 10^{-3}$ mol) and 3.43 g of benzoic anhydride, is heated on an oil bath at 180° C. for 3 hours. The reaction mixture, once returned to room temperature, is washed with ethanol and then with ether. The residue (1.92 g) is recrystallized from 95 ml of dimethylformamide. A 97% pure product is obtained in the form of yellow crystals which is converted at 305° C. into a liquid crystal phase. Amount obtained: 1.59 g, i.e. $3.9 \times 10^{-3}$ mol; yield: 61%.

EXAMPLE 3

Preparation of 6,6'-di(4hydroxystyryl)-3,3-bipyridine

The same operating conditions are used as in Example 1.

The mixture, composed of 943.1 mg of 6,6'-dimethyl-3,3'-bipyridine (DMBP), i.e. $5.12 \times 10^{-3}$ mol, 2.75 g of 4-hydroxybenzaldehyde ($22.5 \times 10^{-3}$ mol) and 2.75 g of benzoic anhydride, is heated on an oil bath at 180° C. for 4 hours. The reaction mixture, once returned to room temperature, is washed with ethanol and then with ether. After saponification in a 2N alcoholic sodium hydroxide solution for 15 minutes at 80° C. and precipitation from water, a precipitate (1.01 g) is recrystallized from 75 ml of dimethylformamide. A 98% pure product is obtained which exhibits a conversion into a liquid crystal phase. Amount obtained: 942 mg, i.e. $2.4 \times 10^{-3}$ mol; yield: 47%.

EXAMPLE 4

Preparation of 6-(4-hydroxystyryl)-6'-(4-cyanostyryl)-3,3'-bipyridine

The first stage in the synthesis is carried out under the same conditions as in Examople 1, with 799.6 mg of 6,6'-dimethyl-3,3'-bipyridine (DMBP), i.e. $4.3 \times 10^{-3}$ mol. 569.0 mg of 4-cyanobenzaldehyde ($4.3 \times 10^{-3}$ mol) and 1.5 g of benzoic anhydride ($6.6 \times 10^{-3}$ mol). The mixture is heated on an oil bath at 140° C. under a slight stream of inert gas for 3 hours. The reaction mixture, once returned to room temperature, is washed with ethanol and then with ether. 530 mg of 4-hydroxybenzaldehyde ($4.3 \times 10^{-3}$ mol) and 1.21 g of benzoic anhydride ($5.3 \times 10^{-3}$ mol) are successively added to the residue. The mixture is heated on an oil bath at 160° C. under a slight stream of inert gas for 10 hours. The reaction mixture, once returned to ambient temperature, is washed with ethanol and then with ether. After saponification in a 2N alcoholic sodium hydroxide solution for 15 minutes at 80° C. and precipitation from water, an 82% pure abovementioned product is obtained. Amount obtained: 351.7 mg, i.e. $9 \times 10^{-4}$ mol,; yield: 21%.

What is claimed is:

1. A polymeric material obtained by homopolymerization, copolymerization or grafting as a side chain onto a constituent unit of a homopolymer or copolymer, or grafted onto a monomer which is then polymerized or copolymerized, of a compound of formula I:

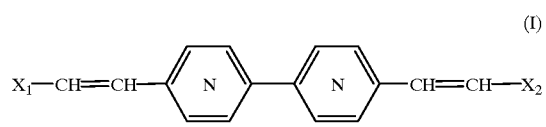

wherein the entity

represents a nitrogenous aromatic heterocyclyl radical comprising 1 to 4 nitrogen atoms chosen from pyridinyl, pyrazinyl, pyrimidinyl or triazinyl and containing at least one nitrogen atom in the α position with respect to the CH=CH double bond, $X_1$ and $X_2$ are, independently of one another, conjugated aliphatic systems themselves conjugated with the remainder of the molecule, or aromatic cyclic or aromatic heterocyclic systems, which are unsubstituted or substituted one or more times with radicals chosen from the following group: alkyl, halo, phenyl, naphthyl, hydroxyl, alkoxy, amino, lower alkylamino, lower dialkylamino, lower alkyl(lower alkoxy)amino, (lower alkylacyl)aminocarbonyl, lower alkylcarbonyl, lower alkoxycarbonyl, carboxyl, (lower alkylamino) carbonyl, (lower dialkylamino)carbonyl, halocarbonyl, trifluoromethyl, nitro, nitroso, cyano, 2,2-dicyanovinyl, 3,3-dicyanoprop-2-enyl, tricyanovinyl, dicyanomethylidenyl, mercapto, alkylthio, sulfino, alkylsulfonyl, sulfo, alkylsulfonyloxy, alkylsulfinyl, pyridinyl and conjugated pyridinyl derivatives.

2. The polymeric material of claim 1 wherein the compound of formula I has a functionality greater than or equal to 1 and the compound of formula I is grafted as the side chain.

3. The polymeric material of claim 2 wherein the compound of formula I is grafted as the side chain onto a polyolefin, polyester, polyamide, poly(vinyl acetate), poly (vinyl chloride), polyurethane, poly(methyl methacrylate) or hydroxyethylcellulose.

4. The polymeric material of claim 1 wherein the compound of formula I has a functionality greater than or equal to 2 and the polymeric material is obtained by homopolymerization or copolymerization.

* * * * *

UNITED STATES PATENT AND TRADEMARK OFFICE
CERTIFICATE OF CORRECTION

PATENT NO. : 6,051,669
DATED : April 18, 2000
INVENTOR(S) : Andre-Jean ATTIAS et al It is certified that error appears in the above-identified patent and that said Letters Patent is hereby corrected as shown below:

On the title page, item [73] should read:

Office National D'Etudes et de Recherches
Aerospatiales (ONERA),
Chatillon, France Signed and Sealed this Tenth Day of April, 2001

Attest:

NICHOLAS P. GODICI

Attesting Officer     Acting Director of the United States Patent and Trademark Office